United States Patent [19]

Resnick

[11] 4,153,720

[45] May 8, 1979

[54] 3-ACYL-5-ALKYL-2H-PYRAN-2,4,6-(3H,5H)-TRIONES AND THEIR 4-HYDROXY TAUTOMERS

[75] Inventor: Theodore M. Resnick, Bala Cynwyd, Pa.

[73] Assignee: SmithKline Corporation, Philadelphia, Pa.

[21] Appl. No.: 870,792

[22] Filed: Jan. 19, 1978

[51] Int. Cl.$^2$ .................. A61K 31/35; C07D 309/22
[52] U.S. Cl. .......................... 424/283; 260/345.9 R
[58] Field of Search .............. 260/345.9 R; 424/283

[56] References Cited

U.S. PATENT DOCUMENTS 4,025,614  5/1977  Snader et al. .............. 260/345.9 R

FOREIGN PATENT DOCUMENTS 835266  5/1976  Belgium ..................... 260/345.9 R

OTHER PUBLICATIONS

Kiang et al., J. Chem. Soc., 2721 (1971).

Primary Examiner—Nicky Chan
Attorney, Agent, or Firm—William H. Edgerton

[57] ABSTRACT

3-Acyl-5-alkyltetrahydro-2,4,6-pyrantriones are prepared by catalytic hydrogenation of their 3,5-diacyl congeners. They have been found to have anti-allergic activity useful for treating the symptoms of asthma.

6 Claims, No Drawings

3-ACYL-5-ALKYL-2H-PYRAN-2,4,6-(3H,5H)-TRIONES AND THEIR 4-HYDROXY TAUTOMERS

This invention comprises a group of partially hydrogenated diacetyltetrahydropyrantriones which have biological activity especially anti-allergic activity. The structures of these compounds are distinguished by having a lower alkanoyl and a lower alkyl group substituted at the 3,5-positions of a tetrahydro-2,4,6-pyrantrione nucleus.

More specifically the structures of the compounds of this invention are illustrated by the following structural formula:

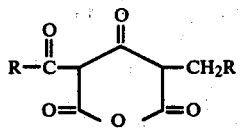

I in which: R is a straight or branched lower alkyl of 1-6 carbon atoms. Preferably R is methyl or ethyl.

PRIOR ART STATEMENT

To the best of my knowledge I am not aware of any tetrahydro-2,4,6-pyrantriones having alkanoyl, alkyl substitution at the 3,5 positions respectively. The starting materials of the preparation of the end product compounds of this invention have 3,5-dialkanoyl substitution and are known to the art, Belgian Pat. No. 835,266 granted May 5, 1976.

The compounds of this invention include compounds possessing either of the tautomeric forms of the 4-keto group.

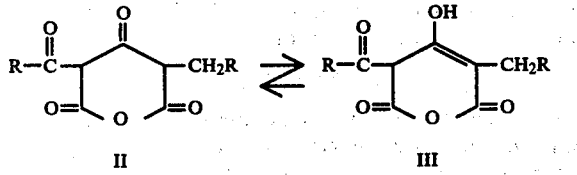

II          III

In practice it is convenient to produce the keto form of the tautomer and convert this to the enol form by equilibration in an organic solvent with added base.

The compounds of this invention are unexpectedly prepared by catalytic hydrogenation of the corresponding 3,5-dialkanoyltetrahydropyranetrione:

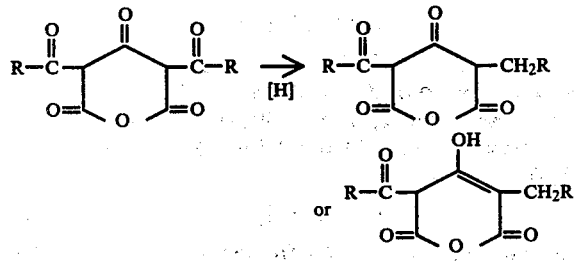

The hydrogenation is most conveniently carried out in an organic solvent in which the diacyltrione is substantially soluble most conveniently aqueous alcohol such as aqueous ethanol or methanol. The pressure of the hydrogen atmosphere is again most conveniently within the conventional low pressure range such as from 40-70 psi. The catalyst is critical with common noble metal supported on carbon catalysts most useful for preparing the keto products (I above). The nobel metal catalysts which are very useful are the various forms of palladium, platinum or rhodium on carbon known to the art.

Unexpectedly when the catalyst is prereduced platinum oxide or palladium black, the product is the enol form of the tautomer (II). Room temperatures are usually but not always used and the hydrogenation is continued until the theoretical uptake of hydrogen is complete. The products are isolated by conventional chemical techniques as will be obvious from the illustrative examples.

It is surprising that no hydrogenation of the tautomeric olefinic centers occurs during the reaction.

The enol tautomeric form is also prepared from the keto form by dissolving the latter in aqueous ethanol with a small amount of base such as organic base, for example triethylamine, tributylamine or pyridine.

The compounds of this invention and their pharmaceutical compositions inhibit the release and/or formation of pharmacologically active mediators from effector cells triggered by the interaction of antigen and a specific antibody fixed to the cell surface. Thus the anti-allergic compounds of this invention are therefore valuable in the treatment of allergic diseases such as asthma, rhinitis and urticaria.

The inhibitory activity of the compounds of this invention on mediator release in sensitized tissues is measured by the ability of the active medicament to inhibit the passive cutaneous anaphylaxis (PCA) reaction in rats. In this test system, titered and appropriately diluted serum (from rats previously immunized by the intraperitoneal injection of ovalbumin aluminum hydroxide or ovalbumin-i.m.-Bordatella pertussis U.S.P. (i.p.)-and N. Brasiliensis (i.p.) containing reaginic antibodies directed against ovalbumin is injected intradermally at four sites on the shaved backs of normal adult male rats. Forty-eight hours later the animals are injected intravenously with 0.5 ml. of isotonic saline solution containing 5 mg. of the ovalbumin antigen and 5 mg. of Evans blue dye. Chemical mediators such as histamine and serotonin which are released at the sensitized sites as a result of a local cellular anaphylaxis, cause an increase in capillary permeability with resultant leakage of plasma and formation of a wheal. The wheal is visualized by the plasma protein-bound Evans blue dye. Under conditions of the test, the average control wheal is approximately 12×12 mm. Thirty minutes following antigen challenge, the animals are killed, the dorsal skin is reflected and the diameter of the wheals recorded. A test compound is administered intravenously, initially at 0.5 minutes prior to antigen challenge (longer pretreatment times and other routes of drug administration, i.e. oral or intraperitoneal, may be employed). Percent inhibition is calculated from the difference in mean average wheal diameter between a treated group and saline or appropriate diluent controls.

The compounds of Formulas II and III are administered intravenously to rats at doses of from 5 to 15 mg/kg produce marked inhibition of the PCA reaction. A representative compound 3-acetyl-5-ethyl-2H-pyran-2,4,6-[3H,5H]-trione, produced 43% inhibition of the rat PCA wheal at 5 mg/kg i.v. 3-Acetyl-5-ethyl-4-hydroxy-2H-pyran-2,6-(3H)-dione at 5 mg/kg. i.v. gave a 42% inhibition of wheal. 4-Hydroxy-3-propionyl-5-propyl-2H-pyran-2,6-(3H)-dione at 5 mg/kg i.v. gave a 30% reduction in wheal.

This general test procedure and the comparative results obtained with the standard commercial antiallergic product, disodium chromoglycate, are disclosed in J. Goose et al., Immunology 16, 749 (1969) and S. I. Ankil, Int. Arch. Allergy 41, 163 (1971).

The pharmaceutical compositions of this invention comprise an appropriate amount of a substituted alkylalkanoyltetrahydropyrantrione as set forth in Formulas I and II in association with a pharmaceutical carrier or diluent. The nature of the composition and the pharmaceutical carrier or diluent will of course depend upon the intended route of administration, i.e. orally, parenterally or by inhalation. Preferably the active medicament is administered to an animal in a composition comprising an amount sufficient to produce an inhibition of the antigen-antibody reaction. When employed in this manner, the dosage of composition is such that from 50 mg to 750 mg of active ingredient are administered at each administration. Advantageously equal doses will be administered 1 to 4 times daily with the daily dosage regimen being about 100 mg to about 3000 mg.

In general, particularly for the prophylactic treatment of asthma, the compositions will be in a form suitable for administration by inhalation. Thus the compositions will comprise a suspension or solution of the active ingredient in water for administration by means of a conventional nebulizer. Alternatively the compositions will comprise a suspension or solution of the active ingredient in a conventional liquefied propellant such as dichlorodifluoromethane or chlorotrifluoroethane to be administered from a pressurized container. The compositions may also comprise the solid active ingredient diluted with a solid diluent, e.g. lactose, for administration from a powder inhalation device. In the above compositions, the amount of carrier or diluent will vary but preferably will be the major proportion of a suspension or solution of the active ingredient. When the diluent is a solid, it may be present in less, equal or greater amounts than the solid active ingredient.

A wide variety of other pharmaceutical forms can be employed. Thus, if a solid carrier is used the preparation can be tableted, placed in a hard gelatin capsule in powder or pellet form, or in the form of a troche or lozenge for oral administration. The amount of solid carrier will vary widely but preferably will be about 25 mg. to about 1 g. If a liquid carrier is used, the preparation will be in the form of a syrup, emulsion, soft gelatin capsule, sterile injectable liquid such as an ampul, or an aqueous or nonaqueous liquid suspension.

Exemplary of solid carriers are lactose, terra alba, sucrose, talc, gelatin, agar, pectin, acacia, magnesium stearate, stearic acid and the like. Exemplary of liquid carriers are syrup, peanut oil, olive oil, water and the like. Similarly the carrier or diluent can include any time delay material well known to the art, such as glyceryl monostearate or glyceryl distearate alone or with a wax.

The method in accordance with this invention also includes inhibiting the effects of the antigen-antibody reaction which comprises the prior application to the area of the antigen-antibody mechanism a therapeutically effective amount of a substituted alkylalkanoyltetrahydropyrantrione of Formulas I or II. A particular application is a method of relieving or preventing allergic airway obstruction which comprises administering to an animal a therapeutically effective amount at suitable intervals.

The pharmaceutical preparations are made following the conventional techniques of the pharmaceutical chemist involving mixing, granulating and compressing when necessary, or variously mixing and dissolving the ingredients as appropriate to the desired end product.

The accompanying examples illustrate the preparation of compounds of Formulas I or II and their incorporation into pharmaceutical compositions of this invention and as such are not to be considered as limiting the invention set forth in the claims appended hereto. All temperatures are in degrees Centigrade.

EXAMPLE 1

A mixture of 2.14 g (0.01 m) of diacetyltetrahydropyrantrione (prepared by the method of J. Chem. Soc., 2721 (1971) and Ann., 273 194 (1893), Belgian Pat. No. 835,266) in 200 ml of ethanol:water (1:3) was shaken at 60 psi of hydrogen in the presence of prereduced platinum oxide catalyst (0.4 g) until hydrogen uptake was complete. The catalyst was removed by filtration. The filtrate was concentrated. The residue was recrystallized from ethyl acetate to give 3-acetyl-5-ethyl-4-hydroxy-2H-pyran-2,6-(3H)-dione, m.p. 212°. The same material was obtained when the catalyst employed was 0.6 g palladium black.

EXAMPLE 2

A mixture of 2.14 g (0.01 m) of diacetyltetrahydropyrantrione in 200 ml of aqueous ethanol was shaken at 60 psi and room temperature with 0.4 g of 5% palladium on charcoal for 1 to 3 hours. Removing the catalyst, evaporation of the filtrate and recrystallization of the residue gave 3-acetyl-5-ethyl-2H-pyran-2,4,6-[3H,5H]-trione, m.p. 152°. Use of 5% platinum on charcoal, 5% rhodium on charcoal or 5% platinum on alumina also gave the same product.

EXAMPLE 3

An equimolar quantity of the dipropionyl congener was reduced using the process of Example 1 to give 4-hydroxy-3-propionyl-5-propyl-2H-pyran-2,6(3H)-dione, m.p. 149°–150°.

EXAMPLE 4

An admixture of the products of Examples 1 and 2 was dissolved in aqueous methanol at room temperature with a drop of triethylamine. Evaporation gives the enolic form of Example 1.

EXAMPLE 5

A mixture of 2.5 g of di-n-butyryltetrahydropyrantrione (K. Kato et al., J. Chem. Soc. 1969 1997) in aqueous ethanol is hydrogenated at 60 psi with palladium on carbon to give 3-butyryl-5-butyl-2H-pyran-2,4,6-(3H,5H)-trione.

EXAMPLE 6

A mixture of 2 g of 3,5-dihexanoyltetrahydropyrantrione (Belgian Pat. No. 835,266) is hydrogenated with palladium on carbon to give 3-hexanoyl-5-hexyl-2H-pyran-2,4,6-(3H,5H)-trione.

EXAMPLE 7

| Ingredients | Mg/Capsule |
| --- | --- |
| 3-Acetyl-5-ethyl-2H-pyran-2,4,6-[3H,5H]-trione | 150 |
| Magnesium stearate | 5 |

EXAMPLE 7-continued

| Ingredients | Mg/Capsule |
| --- | --- |
| Lactose | 250 |

The above ingredients are screened through a #40 mesh screen, mixed and filled into #0 hard gelatin capsules.

The capsules are administered orally to a subject in need of anti-allergic treatment from 2–5 times daily.

What is claimed is:

1. A compound of the formula:

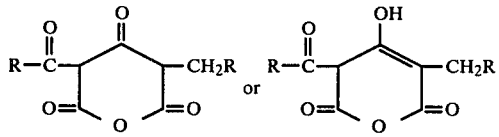

in which R is a lower alkyl of from 1–6 carbon atoms.

2. The compound of claim 1 in which the compound is 3-acetyl-5-ethyl-4-hydroxy-2H-pyran-2,6-(3H)-dione.

3. The compound of claim 1 in which the compound is 3-acetyl-5-ethyl-2H-pyran-2,4,6-[3H,5H]-trione.

4. The compound of claim 1 in which the compound is 4-hydroxy-3-propionyl-5-propyl-2H-pyran-2,6-(3H)-dione.

5. A pharmaceutical composition for inhibiting the symptoms of asthma comprising a nontoxic pharmaceutical carrier and a nontoxic amount sufficient to produce said inhibition of a compound of claim 1.

6. The method of inhibiting the symptoms of asthma which comprises administering to a subject in need thereof a therapeutically effective amount for producing said inhibition of a compound of claim 1.

* * * * *